(12) United States Patent
Lefki et al.

(10) Patent No.: US 7,108,690 B1
(45) Date of Patent: Sep. 19, 2006

(54) HAIR-REMOVING DEVICE WITH A CONTROLLABLE LASER SOURCE

(75) Inventors: Karim M. T. Lefki, Chartres (FR); Abraham J. Cense, Eindhoven (NL); Xiang S. Cheng, Eindhoven (NL); Willem D. Van Amstel, Eindhoven (NL); Gerrit J. Veldhuis, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1178 days.

(21) Appl. No.: 09/548,730

(22) Filed: Apr. 13, 2000

(30) Foreign Application Priority Data

Apr. 14, 1999 (EP) ................... 99201169

(51) Int. Cl.
*A61B 18/18* (2006.01)
*A61B 18/20* (2006.01)

(52) U.S. Cl. ............... 606/10; 606/9; 606/12; 607/89

(58) Field of Classification Search .......... 606/7–13, 606/127, 131; 128/898; 607/88–91; 345/614, 345/619, 581, 618
See application file for complete search history.

(56) References Cited

U.S. PATENT DOCUMENTS

| | | | | |
|---|---|---|---|---|
| 4,813,412 A | * | 3/1989 | Yamazaki et al. | 128/303.13 |
| 4,901,718 A | * | 2/1990 | Bille et al. | 60/4 |
| 5,049,147 A | * | 9/1991 | Danon | 606/10 |
| 5,653,706 A | * | 8/1997 | Zalvislan et al. | 606/9 |
| 5,995,867 A | * | 11/1999 | Zalvislan et al. | 600/476 |
| 6,074,382 A | * | 6/2000 | Asah et al. | 606/9 |
| 6,104,959 A | * | 8/2000 | Spertell | 607/101 |
| 6,149,644 A | * | 11/2000 | Xie | 606/9 |

(Continued)

FOREIGN PATENT DOCUMENTS

EP 0880941 A1 12/1998

(Continued)

*Primary Examiner*—A. Farah
(74) *Attorney, Agent, or Firm*—Adam L. Stroud (57) ABSTRACT

A hair-removing device (1) includes a laser source (3), an adjustable laser beam manipulator (5) for positioning a laser beam (7) of the laser source (3) in a target position (9) on a skin (11) to be treated, and an image sensor (47) for detecting an image (49) of the skin. The hair-removing device further comprises a control unit (17) which determines a position and orientation on the skin of a hair (13) to be removed, and which determines the target position of the laser beam as a function of said position and orientation of the hair. The control unit brings the laser beam manipulator in a state corresponding to the target position of the laser beam, and activates the laser source when the laser beam manipulator has reached said state. Thus, the hair-removing device is suitable for use by inexperienced users, and is particularly suitable for the consumer market. In a particular embodiment, the control unit determines the target position of the laser beam in a position (71) on the skin under which a root (15) of the hair is present, so that the root of the hair is destroyed and the hair-removing device (1) is an epilating device by means of which the hair is removed for a relatively long time or even permanently. In another embodiment, the control unit determines the target position of the laser beam in a position (65) on the hair where the hair comes out of the skin, so that the hair is burnt through near the skin surface and the hair-removing device (1") is a shaving device by means of which a high skin smoothness is obtained.

2 Claims, 7 Drawing Sheets

U.S. PATENT DOCUMENTS 6,214,034 B1 * 4/2001 Azar ........................... 607/89
6,706,035 B1 * 3/2004 Cense et al. .................... 606/9
6,955,672 B1 * 10/2005 Cense et al. .................... 606/9
6,976,984 B1 * 12/2005 Cense et al. .................... 606/9

FOREIGN PATENT DOCUMENTS

WO  9911324 A1  3/1999

* cited by examiner

HAIR-REMOVING DEVICE WITH A CONTROLLABLE LASER SOURCE

BACKGROUND OF THE INVENTION

The invention relates to a hair-removing device provided with a laser source, an adjustable laser beam manipulator for positioning a laser beam supplied by the laser source during operation in a target position on a skin to be treated, and an image sensor for detecting an image of at least a portion of the skin.

A hair-removing device of the kind mentioned in the opening paragraph is known from U.S. Pat. No. 5,653,706. The known hair-removing device is designed for use by a professional therapist and may be used not only for removing hairs but also for other dermatological treatments such as the treatment of necrotic skin tissue, varicose veins, or pigment spots. The image of the skin detected by the image sensor is rendered visible to the therapist on a picture screen. The known hair-removing device further comprises a control member by means of which the therapist can operate the laser beam manipulator and can thus guide the laser beam supplied by the laser source manually over the skin under treatment. While being guided over the skin, the laser beam has only a comparatively low energy density, and the therapist can monitor the position of the laser beam on the skin by means of the picture screen. When the laser beam is in the target position as determined by the therapist, the laser beam can be intensified for a predetermined time duration by the therapist through the operation of a further control member of the hair-removing device. The laser beam has a wavelength which is well absorbed by the tissue to be treated, so that the tissue present around the target position is strongly heated locally by the laser beam, and the relevant tissue dies. For a permanent removal or epilation of a hair present on the skin, the laser beam is aimed at the root of the hair, so that the root and the tissue surrounding it die. Since the known hair-removing device is provided with said image sensor and adjustable laser beam manipulator, it is possible to treat the skin locally with a laser beam of a comparatively small spot diameter, so that the laser source need have only a comparatively low power. Accordingly, a comparatively small and simple laser diode is used in the known hair-removing device.

A disadvantage of the known hair-removing device is that a comparatively long treatment time is necessary for the removal of all hairs present on a skin under treatment because the therapist must displace the laser beam manually from one hair to the next. In addition, a determination of the target position of the laser beam on the skin requires the user to have a considerable experience, so that the known hair-removing device is suitable exclusively for use by a professional therapist.

SUMMARY OF THE INVENTION

It is an object of the invention to provide a hair-removing device of the kind mentioned in the opening paragraph with which a comparatively short treatment time is possible and which is suitable for use by inexperienced persons, i.e. suitable for the consumer market.

To achieve this object, a hair-removing device according to the invention is characterized in that the laser source is controllable by means of an electrical control unit, which control unit during operation determines the target position of the laser beam as a function of a position and/or orientation on the skin of a hair to be removed as determined from the image by the control unit, and which control unit activates the laser source the moment the laser beam manipulator is in a position which corresponds to the target position of the laser beam. The determination of the target position of the laser beam and the activation of the laser source take place fully automatically because the target position of the laser beam is determined by the control unit and the laser source is activated by the control unit when the laser beam manipulator is in a position which corresponds to the target position of the laser beam. The control unit also renders it possible, for example, to adjust the laser beam manipulator in a predetermined manner automatically in that position which corresponds to the target position of the laser beam on the skin. This renders the hair-removing device according to the invention suitable for a safe use by inexperienced persons, so that the hair-removing device is particularly suitable for the consumer market. The control unit comprises, for example, a suitable algorithm for determining the target position for the laser beam from the image of the skin detected by the image sensor, which algorithm is capable of determining the position and/or the orientation of the hair to be removed on the skin on the basis of the image information and is capable of determining the target position on the basis of said position and/or orientation of the hair. The automatic determination of the target position of the laser beam as described above, the automatic adjustment of the laser beam manipulator, and the automatic activation of the laser source take place within a comparatively short time, so that a comparatively short treatment period can be achieved by means of the hair-removing device according to the invention.

A special embodiment of a hair-removing device according to the invention is characterized in that the control unit determines the target position of the laser beam in a partial region of the image having dimensions which are determined by a previously determined average distance between hairs present on the skin and a previously determined length of the hairs. In this special embodiment, the control unit is active substantially exclusively in said partial region of the image which comprises no more than a few hairs to be removed and preferably only a single hair. Said previously determined length of the hairs should preferably be smaller than said average distance between the hairs and can be achieved, for example, in that the hairs are trimmed by means of a separate trimmer or, for example, a trimmer belonging to the hair-removing device prior to the treatment by means of the hair-removing device. Since the control unit is active substantially exclusively in said partial region of the image, a calculation time and calculation capacity of the control unit required for determining the target position are strongly reduced.

A further embodiment of a hair-removing device according to the invention is characterized in that the dimensions of the partial region of the image are adjustable. Since the dimensions of the partial region of the image are adjustable, said dimensions can be adapted to the properties of the skin under treatment by the user of the hair-removing device, so that the treatment time and treatment result can be optimized for each individual user.

A yet further embodiment of a hair-removing device according to the invention is characterized in that the laser beam manipulator is adjustable by means of the control unit into a sequence of consecutive positions which correspond to a regular sequence of virtual positions of the laser beam on said portion of the skin, a reference position in the partial region of the image corresponding to the instantaneous virtual position of the laser beam, and the control unit activating the laser source when the reference position corresponds to the target position of the laser beam. In this yet further embodiment, the portion of the skin corresponding to the image is scanned by the laser beam manipulator in a regular manner. Since the reference position lying in the partial region of the image corresponds to the instantaneous virtual position of the laser beam, the partial region of the image will follow the instantaneous virtual position of the laser beam, so that the target position in the partial region of the image as determined by the control unit changes continually with respect to the reference position. An advantage of this yet further embodiment is that the laser beam manipulator is continuously justed in a regular manner by the control unit, so that the laser beam manipulator need not have an exceptionally short adjustment time and an exceptionally high adjustment accuracy.

A special embodiment of a hair-removing device according to the invention is characterized in that the control unit determines the target position of the laser beam in a regular sequence of consecutive partial regions of the image, the laser beam manipulator being adjustable by means of the control unit in each of said partial regions into a position which corresponds to the target position of the laser beam in the relevant partial region. In this special embodiment, the detected image of the skin is scanned by the control unit in a regular manner in accordance with said sequence of consecutive partial regions. The control unit determines a target position in each of the consecutive partial regions, whereupon the laser beam manipulator is adjusted into the position corresponding to the relevant target position by the control unit. An advantage of this special embodiment is that the laser beam manipulator need not scan the full portion of the skin which corresponds to the image but is merely adjusted consecutively into positions which correspond to the target positions as determined in the consecutive partial regions of the image. It is true that the laser beam manipulator is adjusted in an irregular manner by the control unit here, so that comparatively high requirements are imposed on the adjustment time and the adjustment accuracy of the laser beam manipulator, but the treatment time of the hair-removing device is considerably further reduced.

A further embodiment of a hair-removing device according to the invention is characterized in that the control unit determines from the position and orientation on the skin of the hair to be removed, as determined from the image, a region on the skin below which a root of the hair will be present with a predetermined degree of probability, the control unit determining at least one target position on the skin in said region. In this further embodiment, the hair-removing device is used as an epilation device. Since the laser beam treats the root of the hair, the root of the hair will die, as will the skin tissue present in the immediate vicinity, so that the hair is permanently removed, or at least for a longer period. The region on the skin below which the root is deemed to be present with the predetermined degree of probability is determined by the control unit on the basis of, for example, previously determined statistical information on the length of the subcutaneous portions of hairs and on the angle of the subcutaneous portions of hairs with respect to the skin surface.

A yet further embodiment of a hair-removing device according to the invention is characterized in that the laser beam manipulator is adjustable by means of the control unit into a sequence of consecutive positions which correspond to a displacement of the laser beam over a rectilinear path on the skin with a predetermined velocity, said rectilinear path lying on a virtual straight line which coincides substantially with a perpendicular projection of the hair to be removed on the skin, the control unit activating the laser source at the start of said displacement. The region on the skin mentioned above below which the root of the hair will be present with the predetermined degree of probability can thus be efficiently treated in its entirety, while a required spot diameter of the laser beam is considerably reduced.

A particular embodiment of a hair-removing device according to the invention is characterized in that the laser beam manipulator is adjustable by means of the control unit into a number of consecutive fixed positions corresponding to a number of fixed target positions of the laser beam on a rectilinear path on the skin, which rectilinear path lies on a virtual straight line which coincides substantially with a perpendicular projection of the hair to be removed on the skin, the control unit activating the laser source in each of said fixed positions of the laser beam manipulator during a predetermined time. Said region on the skin below which the root of the hair will be present with the predetermined degree of probability can thus likewise be efficiently treated in its entirety, while a required spot diameter of the laser beam is likewise strongly reduced.

A further embodiment of a hair-removing device according to the invention is characterized in that the control unit determines an exit position on the hair, where the hair issues from the skin, from the position and orientation on the skin of the hair to be removed as determined from the image, the control unit equalizing the target position of the laser beam with a position on the hair adjacent said exit position. This further embodiment of the hair-removing device is used as a shaver. Since the target position of the laser beam lies on the hair adjacent the exit position of the hair, the hair will be burnt through by the laser beam adjacent the exit position, i.e. adjacent the skin surface. The control unit may be programmed, for example, such that the target position lies at a level with the skin surface, or even below the skin surface, so that a very smooth shaving result is obtained which is maintained for a comparatively long period. The hair-removing device may be provided, for example, with a further adjustment member for adjusting the target position relative to the skin surface, so that the user can set a desired smoothness.

A still further embodiment of a hair-removing device according to the invention is characterized in that the hair-removing device comprises a separate illumination member for illuminating at least the portion of the skin which is to be detected by the image sensor. The use of the separate illumination member achieves that the image detected by the image sensor is fully formed by light from the illumination member reflected by the skin, and the laser source can be completely switched off between the exposures of two consecutive target positions. Reflected light coming from the laser beam need not reach the image sensor because the image detected by the image sensor is fully formed by light of the illumination member reflected by the skin. Accordingly, the image sensor may be provided with a filter for the reflected light of the laser beam, so that the image sensor is protected against damage which may arise as a result of the reflected light of the laser beam when the laser beam is in its target position and has a high energy density.

A special embodiment of a hair-removing device according to the invention is characterized in that the control unit determines from the image a reflection spectrum of the skin portion detected by the image sensor, the control unit comparing the reflection spectrum with a predetermined reference spectrum of at least one frequently occurring skin deviation, while the control unit determines from said comparison positions on the skin in which said skin deviation is present and does not activate the laser source in said positions on the skin. It is prevented in this special embodiment that the laser beam is aimed at target positions which lie within such a skin deviation such as, for example, a mole or some other pigment spot. Such skin deviations often have a comparatively high absorption power for the laser light used for the treatment of the hairs or hair roots, so that injuries arise in the case of contact with laser light. This special embodiment thus provides an automatic protection from such injuries.

A further embodiment of a hair-removing device according to the invention is characterized in that the control unit comprises means for determining an actual position of the laser beam on the skin from the image detected by the image sensor. Since the actual position of the laser beam on the skin is determined, the laser beam manipulator can, for example, be corrected or calibrated in such a manner that said actual position accurately corresponds with the desired target position determined by the control unit. Since said actual position is determined by the image sensor, a separate sensor for determining said actual position is not necessary, and the image sensor is used in an effective manner.

A yet further embodiment of a hair-removing device according to the invention is characterized in that the laser beam manipulator is adjustable by means of the control unit via an output signal of the control unit in accordance with a predetermined mathematical relation between said output signal and the target position, the control unit comprising a calibration member for calibrating said predetermined mathematical relation on the basis of a measured relation between said output signal and the actual position of the laser beam on the skin. Since the control unit adjusts the laser beam manipulator in accordance with said predetermined mathematical relation between said output signal and the target position, the output signal required to achieve a predetermined target position can be determined by the control unit in a relatively short time period, so that the predetermined target position is achieved in a relatively short time period. Since said mathematical relation is calibrated on the basis of a measured relation between said output signal and said actual position, the laser beam is very accurately positionable in the target position by the laser beam manipulator, so that damage of the skin around the target position by the laser beam is prevented as much as possible, and the target position is not missed by the laser beam.

A particular embodiment of a hair-removing device according to the invention is characterized in that, for determining the actual position of the laser beam on the skin, the control unit activates the laser source at a comparatively low energy density. When the laser source is activated at a low energy density, the laser beam generates a spot on the skin which is sufficiently bright to be detected by the image sensor, but which does not damage nor irritate the skin. Thus, the actual position of the laser beam on the skin can be determined by the control member of the control unit in a safe and reliable manner, and the energy consumption of the laser source is considerably limited.

BRIEF DESCRIPTION OF THE DRAWINGS

The invention will be explained in more detail below with reference to the drawing, in which FIG. 1 diagrammatically shows a hair-removing device according to the invention.

DESCRIPTION OF THE EMBODIMENTS

Figure 1:
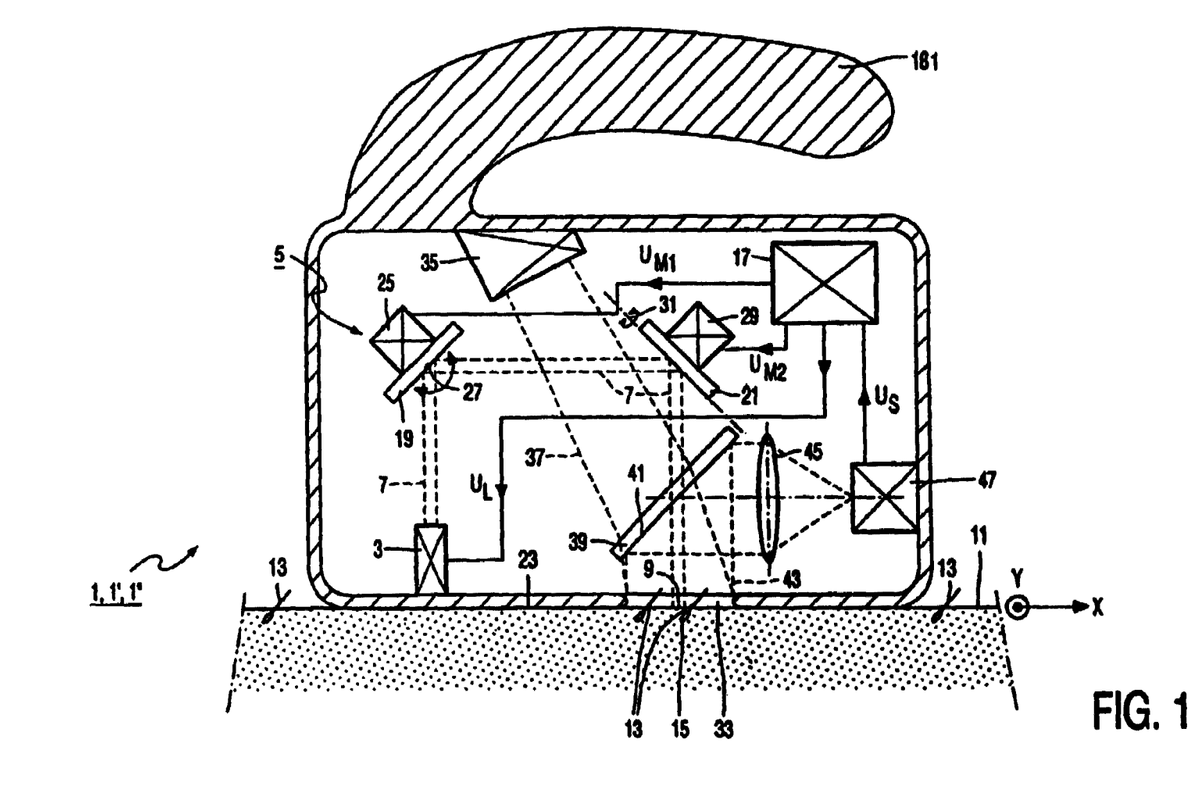
Figure 2:
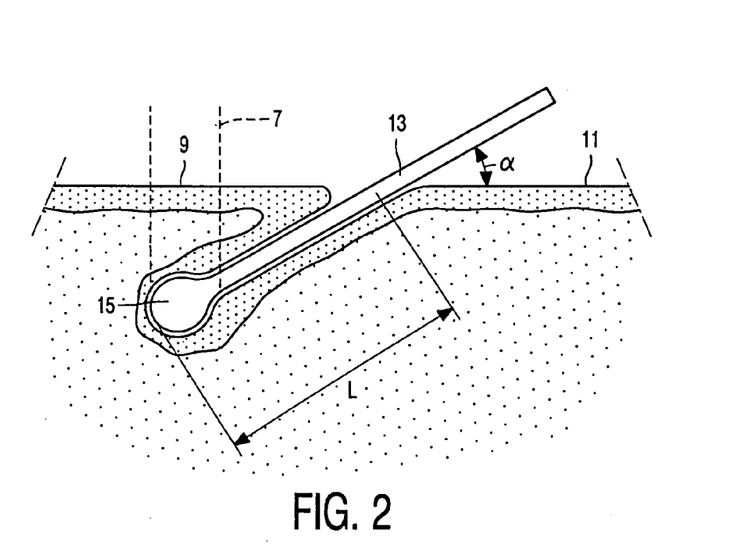
FIG. 2 is a diagrammatic cross-section of a skin to be treated adjacent a hair which is to be removed by means of the hair-removing device of FIG. 1, FIG. 3 diagrammatically shows an image of a portion of a skin under treatment which is detected by means of an image sensor of the hair-removing device of FIG. 1, FIG. 4 diagrammatically shows a control unit of the hair-removing device of FIG. 1, FIG. 5a diagrammatically shows a partial region of the image of FIG. 3, FIG. 5b diagrammatically shows a partial region of the image of FIG. 3 in an alternative embodiment of a hair-removing device according to the invention.

The hair-removing device 1 according to the invention diagrammatically shown in FIG. 1 comprises a laser source 3 and an adjustable laser beam manipulator 5 for positioning a laser beam 7 supplied during operation by the laser source 3 in a target position 9 on a skin 11 to be treated. The hair-removing device 1 is an epilation device by means of which hairs 13 present on the skin 11 can be removed for a comparatively long period or even permanently. If a hair 13 is to be epilated, the target position 9 of the laser beam 7 must be approximately in a position on the skin 111 below which a root 15 of the hair 13 is present, as is diagrammatically shown in FIG. 2. The laser beam 7 contains monochromatic light with a wavelength which is well absorbed by the hair 13 and is substantially not absorbed by tissue of the skin 11. The result of this is that it is substantially exclusively the root 15 of the hair 13 which is strongly heated by the laser beam 7, so that the root 15 dies. A good optical selectivity between the hairs 13 and the tissue of the skin 111 is achieved with a wavelength between approximately 650 nm and 1200 nm in the case of a white skin with dark hairs. Light with such a wavelength is well absorbed by melanin, a pigment which occurs in a high concentration in dark hairs and only in a low concentration in a white skin. Light with such a wavelength is also badly absorbed by water, by hemoglobin, a red pigment which occurs in a high concentration in blood, and by keratin, a substance which occurs in a high concentration in both the outer skin (epidermis) and in the skin tissue which occurs at a lower depth in the skin, where the roots 15 of the hairs 13 are present. A sufficient pulse duration and energy density of the laser beam 7 are furthermore necessary for achieving an effective operation of the hair-removing device 1. A too short pulse duration leads merely to a heating of the root 15 and not to a heating of the tissue present in the immediate vicinity of the root 15. The result is that said tissue remains intact, so that a new root and hair can develop. A too long pulse duration leads to an excessive heating of the tissue present at some distance from the root 15 owing to thermal conduction, which may give rise to skin irritation or even skin damage. Good results are obtained with a pulse duration of the laser beam 7 of between approximately 1 ms and 100 ms and an energy density of the laser beam 7 of between approximately 15 J/cm² and 50 J/cm².

The laser beam 7 can be accurately positioned in the target position 9 by means of the laser beam manipulator 5 in a manner to be described in more detail below, while the target position 9 can be accurately determined by means of an electrical control unit 17 of the hair-removing device 1 in a manner to be described in more detail below. As a result, the laser beam 7 need have only a comparatively small spot diameter for heating the root 15. Good results are obtained at a spot diameter of the laser beam 7 of between approximately 0.3 mm and 1.0 mm. This comparatively small spot diameter means that the laser source 3 need have only a comparatively low output power of a few watts for achieving the required energy density and pulse duration of the laser beam 7. The laser source 3 used in the hair-removing device 1 accordingly comprises only a comparatively small and simple laser diode which is known per se and which is not shown in detail in FIG. 1, or a series of fiber-coupled laser diodes which are known per se and are also not shown in detail in FIG. 1. The laser source 3 further comprises a collimator lens system which is also not shown in FIG. 1 and by means of which the laser beam 7 is directed so as to be substantially parallel.

As FIG. 1 further shows, the laser beam manipulator 5 comprises a first adjustable tilting mirror 19 and a second adjustable tilting mirror 21 which are both positioned at an angle of approximately 45° with respect to a contact surface 23 with which the hair-removing device 1 is to be laid against the skin 11. The first tilting mirror 19 is tiltable through limited angles about a first tilting axis 21 extending in the plane of the first tilting mirror 19 and parallel to the contact surface 23 by means of an actuator 25 which is depicted diagrammatically only in FIG. 1. The second tilting mirror 21 is tiltable through limited angles about a second tilting axis 31 lying in the plane of the second tilting mirror 21 and crossing the first tilting axis 27 approximately perpendicularly by means of an actuator 29 which is also depicted diagrammatically only in FIG. 1. The laser beam 7 supplied by the laser source 3 during operation is reflected by the first tilting mirror 19 and the second tilting mirror 21 through angles of approximately 45°, so that the laser beam 7 hits the skin 11 under treatment substantially perpendicularly in the target position 9 through an opening 33 provided in the contact surface 23. It is noted that the opening 33 may be covered by means of a cover plate of a transparent material. The target position 9 of the laser beam 7 on the skin 11 is displaceable parallel to an X-direction, which lies in the contact surface 23 and which crosses the first tilting axis 27 perpendicularly, in that the first tilting mirror 19 is tilted about the first tilting axis 27 by the actuator 25. The target position 9 of the laser beam 7 on the skin 11 is displaceable parallel to a Y-direction, which also lies in the contact surface 23 and is perpendicular to the X-direction, in that the second tilting mirror 21 is tilted about the second tilting axis 31 by the actuator 29.

As FIG. 1 further shows, the hair-removing device 1 comprises a separate illumination member 35 by means of which a portion of the skin 11 under treatment present below the opening 33 is illuminated during operation. The illumination member 35 may be a simple lamp. A light beam 37 supplied by the illumination member 35 during operation falls through a transparent plate 39, which also transmits the laser beam 7, onto said portion of the skin 11. The transparent plate 39 is positioned at an angle of approximately 45° with respect to the contact surface 23 and is provided with a mirroring surface 41 at a side facing the opening 33. A light beam 43 reflected by said portion of the skin 11 is reflected by the mirroring surface 41 through an angle of approximately 90° and focused onto an image sensor 47, a CCD image sensor which is known per se in the embodiment shown, by means of a lens unit 45. The image sensor 47 is thus capable of detecting an image of said portion of the skin 11 present below the opening 33. The use of the illumination member 35 enables the image sensor 47 to detect a clear image of said portion of the skin 11 from the light of the illumination member 35 reflected by the skin 11, so that no reflected light from the laser beam 7 is necessary for detecting said image. This means that the laser source 3 can be fully switched off between the exposures of two consecutive target positions on the skin 11. In addition, the image sensor 47 may be provided with a filter, not shown in FIG. 1, for the reflected light of the laser beam 7, so that the image sensor 47 is protected against damage which may arise as a result of the reflected light of the laser beam 7 when the laser beam 7 is in the target position 9 with a high energy density.

Figure 3:
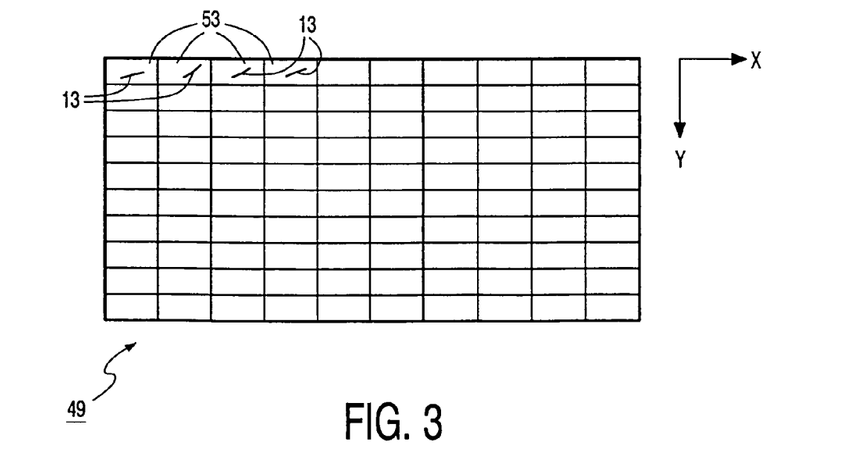
Figure 4:
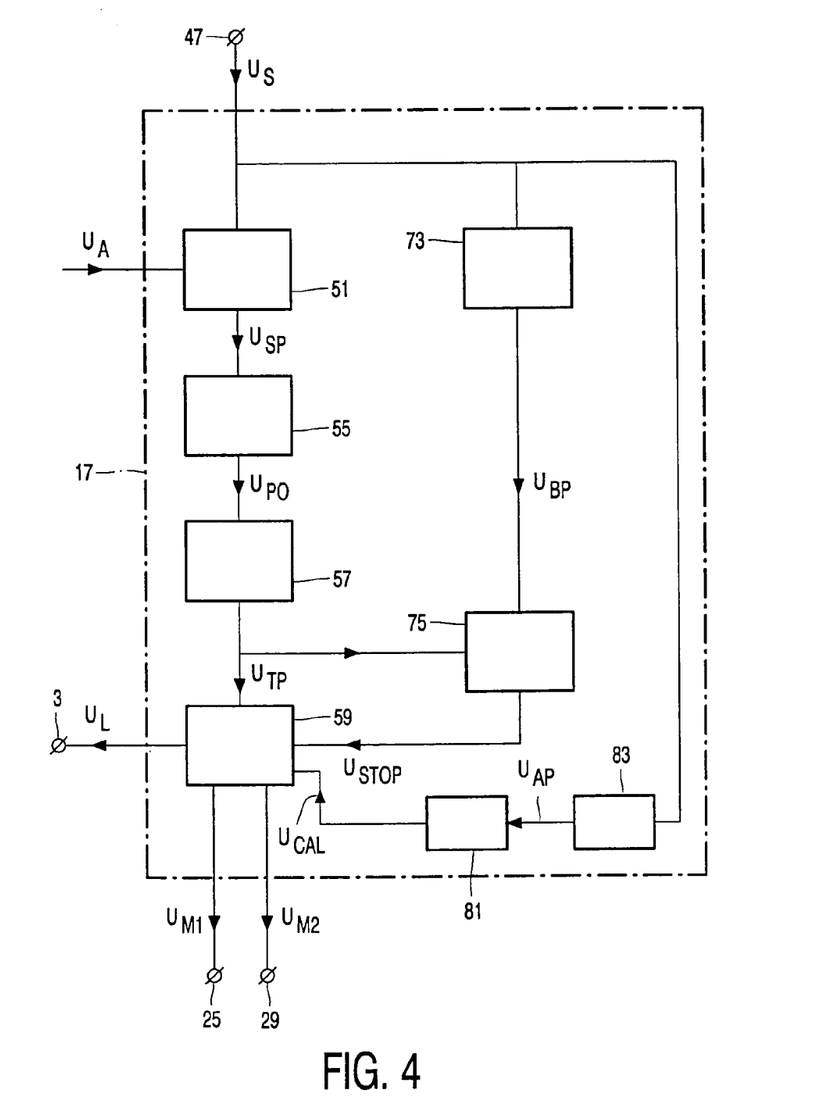

As FIG. 1 shows, the image sensor 47 delivers to the control unit 17 an electrical signal us which corresponds to the image of the portion of the skin 11 present below the opening 33 detected by the image sensor 47, said signal us comprising, for example, a series of 8-bit grey tone values of the image sensor pixels. The detected image is shown diagrammatically in FIG. 3 and indicated with reference numeral 49. As FIG. 4 shows, the control unit 17 comprises a first processor 51, which scans the detected image 49 in a more or less regular manner, said processor 51 generating in succession a number of partial regions 53 of the image 49 as shown in FIG. 3, in particular a more or less regular sequence of partial regions 53 which lie approximately on a number of lines which lie one behind the other as seen in the Y-direction and which extend parallel to the X-direction. The first processor 51 supplies to a second processor 55 of the control unit 17 an electrical signal $u_{SP}$ which corresponds in succession to the partial regions 53 of the image 49 successively generated by the first processor 51. The second processor 55 determines in each partial region 53 the position and the orientation on the skin 11 of the hair or hairs 13 present in the relevant partial region 53, and supplies an electrical signal $u_{PO}$ to a third processor 57 of the control unit 17 which corresponds in succession to the positions and orientations of the hairs 13 in the consecutive partial regions 53 of the image 49 as determined by the second processor 55. The third processor 57 determines in each partial region 53 one or several target positions for the laser beam 7 as a function of said position and orientation of the hair or hairs 13 in the relevant partial region 53 in a manner to be described in more detail below. The partial regions 53 have dimensions which were determined on the basis of a previously determined average distance between the hairs 13 present on the skin 11 and a previously determined length of the hairs 13. In the embodiment shown, the dimensions of the partial regions 53 are such that the partial regions 53 comprise on average only a single hair 13 each. This can be achieved in practice if the user crops the hairs 13 by means of a trimmer prior to the treatment with the hair-removing device 1 to such a length that said previously determined length of the hairs 13 is smaller than said average distance between the hairs 13. Good results are achieved, for example, when the hairs 13 are cropped to a length of between 1 mm and 2 mm for an average distance between the hairs 13 of between 3 mm and 5 mm. It is noted that the first processor 51 generates the consecutive partial regions 53 of the image 49 preferably such that the hair 13 present in a partial region 53 lies approximately in a center of the relevant partial region 53. The sequence of consecutive partial regions 53 then obviously will not have the regularity shown in FIG. 3, but it is more or less regular, with the possibility, for example, of an interspacing being present between consecutive partial regions 53, or with consecutive partial regions 53 lying, for example, not exactly in one line. Since the partial regions 53 on average contain only a single hair 13 each, the position and the orientation of a hair 13 in a partial region 53 and the target positions of the laser beam 7 can be determined within a very short period of time by the second processor 55 of the control unit 17 and by the third processor 57 of the control unit 17, respectively, and a required calculation capacity of the second processor 55 and the third processor 57 can be strongly reduced. Preferably, the hair-removing device 1 further comprises an adjustment member, not shown in the Figures, by means of which the user of the hair-removing device 1 can set the dimensions of the partial regions 53. Said adjustment member for this purpose supplies to the first processor 51 an electrical signal $u_A$ which corresponds to the dimensions set by the user. The user can thus adapt the dimensions of the partial regions 53 to the properties of the skin to be treated, in particular to the average distance between the hairs on the skin and the average length of the cropped hairs, so that the treatment result and the treatment time can be optimized by the individual user.

As FIG. 4 further shows, the third processor 57 supplies an electrical signal $u_{TP}$ to a fourth processor 59 of the control unit 17, which signal corresponds consecutively to the target positions of the laser beam 7 determined by the third processor 57 in the consecutive partial regions 53. The fourth processor 59 determines a first output signal $u_{M1}$ and a second output signal $u_{M2}$ of the control unit 17, by means of which the control unit 17 controls the first tilting mirror 19 and the second tilting mirror 21 of the laser beam manipulator 5, respectively, as a function of the signal $u_{TP}$. The output signals $u_{M1}$ and $u_{M2}$ are determined by the fourth processor 59 such that the tilting mirrors 19 and 21 are adjusted into positions which correspond to the target position of the laser beam 7 in the relevant partial region 53 which corresponds to the signal $u_{TP}$ each time. The fourth processor 59 also supplies a third output signal $u_L$ of the control unit 17 by means of which the control unit 17 controls the laser source 3. The fourth processor 59 delivers the output signal $U_L$ at a predetermined moment after delivering the output signals $u_{M1}$ and $u_{M2}$, said predetermined moment corresponding to a predetermined required adjustment time of the tilting mirrors 19 and 21. The fourth processor 59 supplies the output signal $u_L$ with the predetermined pulse duration, so that the laser beam 7 is active in the relevant target position for the predetermined pulse duration.

The detected image 49 is regularly scanned by the control unit 17 in the manner described above in accordance with said sequence of consecutive partial regions 53, the laser beam manipulator 5 being adjusted by the control unit 17 into consecutive positions only which correspond to the target positions determined in the consecutive partial regions 53. This means that the laser beam manipulator 5 need be adjusted into a limited number of consecutive positions only, so that a particularly short treatment time is obtained by means of the hair-removing device 1. The laser beam manipulator 5, however, is adjusted in a comparatively irregular manner during this, so that comparatively high requirements are imposed on the adjustment accuracy of the laser beam manipulator 5 and on the adjustment time required for achieving a given adjustment accuracy. The fact that the target positions of the laser beam 7 are automatically determined by the control unit 17, and the fact that the laser source 3 is automatically activated by the control unit 17 after the laser beam manipulator 5 has been automatically adjusted into a correct, accurate position corresponding to a given target position by the control unit 17, render the hair-removing device 1 according to the invention particularly suitable for a safe use by inexperienced persons, so that the hair-removing device 1 is particularly suitable for the consumer market. The determination of the target positions of the laser beam 7 yet to be described in more detail below, the automatic adjustment of the laser beam manipulator 5, and the automatic activation of the laser source 3 take place in a comparatively short period of time, so that comparatively short treatment times are possible with the hair-removing device 1 according to the invention.

Figure 5A:
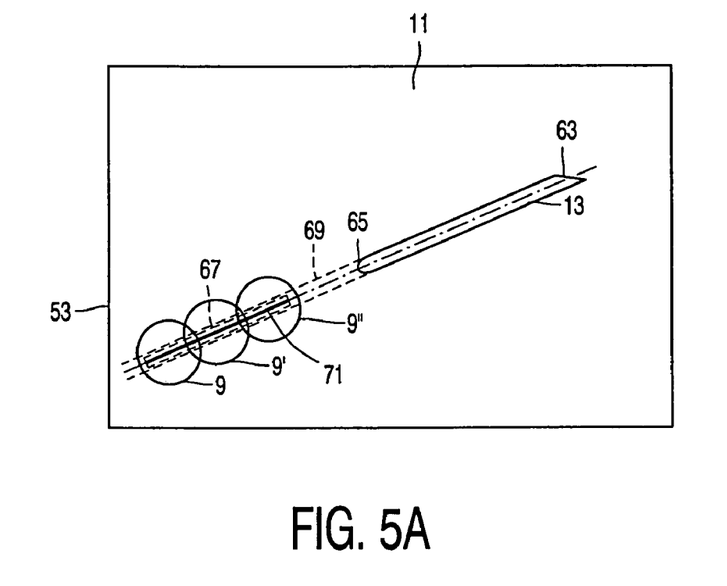

The target positions of the laser beam 7 are determined within a partial region 53 of the detected image 49 by the control unit 17 in the following manner. FIG. 5a diagrammatically shows a partial region 53 in which a hair 13 to be epilated is present. The second processor 55 of the control unit 17 determines from the signal $u_{SP}$ a grey tone distribution for the relevant partial region 53, from which the position and the orientation of the hair 13 on the skin 11 in the partial region 53 are determined. The second processor 55 also draws a distinction between a hair end 63 and a hair exit position 65 where the hair 13 issues from the skin 11. Said distinction is made by means of predetermined grey tone characteristics and shape characteristics of cropped hair ends and hair exit positions which are stored in the memory of the second processor 55. The third processor 57 of the control unit 17 subsequently determines from the position and orientation of the hair 13 and the exit position 65 thus determined a region 67 on the skin 11 below which the root 15 of the hair 13 will be present with a predetermined degree of probability. In the embodiment shown, it is assumed in the determination of said region 67 that the root 15 is present at a virtual rectilinear subcutaneous extension distance 69 of the hair 13, i.e. extending from the detected exit position 65, while it is further assumed that an angle α shown in FIG. 2 between the hair 13 and the surface of the skin 11 and a length L, also shown in FIG. 2, of a portion of the hair 13 present below the surface of the skin 11 lie between certain minimum and maximum values which were previously statistically determined. The region 67 thus determined is elongate and extends along a straight line segment 71 which lies on a virtual line which coincides substantially with a perpendicular projection of the hair 13 on the skin 11. The third processor 57 subsequently determines on the line segment 71 thus determined a number, for example three, of fixed target positions 9, 9', and 9" for the laser beam 7, mutually overlapping by a small portion each time, and the third processor 57 supplies to the fourth processor 59 a number of consecutive signals $u_{TP}$ which correspond to said target positions 9, 9', and 9". As a result of this, the fourth processor 59 of the control unit 17 adjusts the laser beam manipulator 5 into a number of consecutive fixed positions which correspond to the target positions 9, 9', and 9" of the laser beam 7 thus determined, the fourth processor 59 activating the laser source 3 for the predetermined pulse duration in each of the consecutive fixed positions of the laser beam manipulator 5.

Figure 5B:
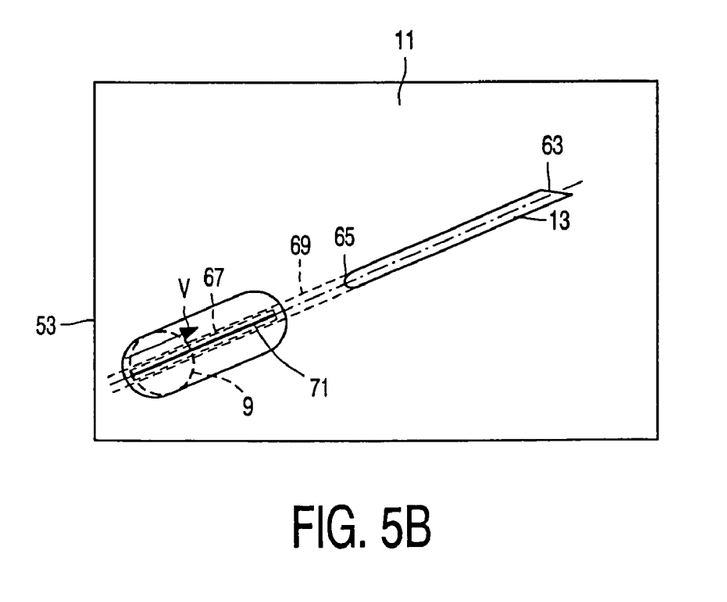

FIG. 5b shows a partial region 53 of the detected image 49 in an alternative embodiment of the hair-removing device 1 according to the invention. In this alternative embodiment, the third processor 57 supplies to the fourth processor 59 a signal $u_{TP}$ which corresponds to a displacement of the laser beam 7 with a predetermined velocity v over said straight line segment 71, so that the fourth processor 59 adjusts the laser beam manipulator 5 into a sequence of consecutive positions which correspond to said displacement of the laser beam 7. The fourth processor 59 of the control unit 17 in this alternative embodiment activates the laser source 3 at the start of said displacement and the fourth processor 59 switches off the laser source 3 at the end of said displacement. To obtain a result in this alternative embodiment comparable to the result achieved by the embodiment shown in FIG. 5a, said predetermined velocity v of the laser beam 7 should be approximately equal to a quotient of the spot diameter of the laser beam 7 and the pulse duration used in FIG. 5a.

Figure 6:
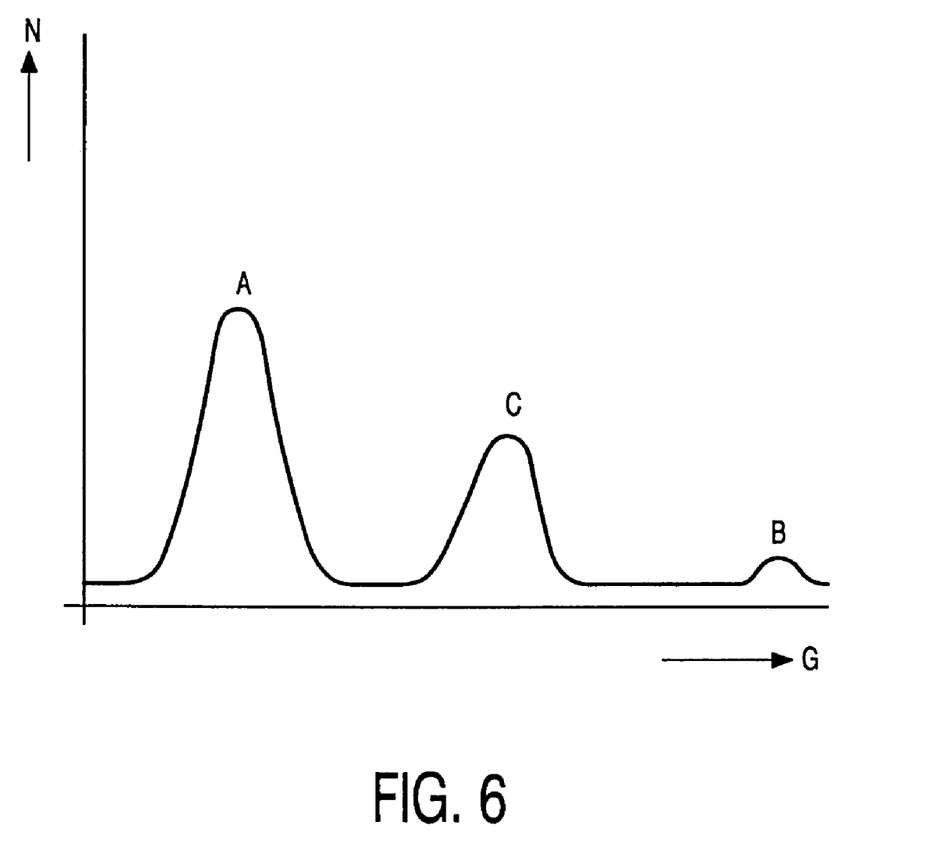
FIG. 6 shows a reflection spectrum determined by the control unit of FIG. 4 from the image of FIG. 3, FIG. 7 diagrammatically shows a control unit of a further embodiment of a hair-removing device according to the invention, FIG. 8 diagrammatically shows a partial region of a detected image of the skin under treatment generated by the control unit of FIG. 7, and FIG. 9 diagrammatically shows a partial region of an image of the skin under treatment generated by a control unit of a yet further embodiment of a hair-removing device according to the invention.

In the embodiment shown in FIG. 4, the control unit 17 further comprises a fifth processor 73 which determines a reflection spectrum of the portion of the skin 11 present below the opening 33 from the image 49 detected by the image sensor 47, i.e. from the signal $u_S$, and which compares this reflection spectrum with a predetermined reference spectrum which is stored in a memory of the fifth processor 73 and which contains information characteristic of at least one frequently occurring skin deviation. FIG. 6 shows an example of such a reflection spectrum, wherein the horizontal axis represent a measured grey tone G and the vertical axis a number of image sensor pixels N. The reflection spectrum shown comprises a first, comparatively great peak A with grey tones corresponding to a white skin, a second, comparatively small peak B with grey tones corresponding to dark hairs, and a third peak C with grey tones corresponding to said skin deviation. The fifth processor 73 determines from said comparison the positions on the skin 11 where said skin deviation occurs and supplies to a sixth processor 75 of the control unit 17 an electrical signal $u_{BP}$ which corresponds to the positions on the skin 11 of said skin deviation thus determined. The sixth processor 75 compares the signal $u_{TP}$, which corresponds to a target position of the laser beam 7 determined by the third processor 57, with the positions on the skin 11 of said skin deviation thus determined, and supplies a signal $u_{STOP}$ to the fourth processor 59 whenever the target position of the laser beam 7 coincides with one of the positions of said skin deviation on the skin 11. When the fourth processor 59 receives the signal $u_{STOP}$, the laser source 3 is not activated by the fourth processor 59. The use of the fifth processor 73 and the sixth processor 75 prevents the laser beam 7 from being active in positions on the skin 11 where said skin deviation is present. Examples of this are moles or other pigment spots. Such skin deviations have a comparatively high absorption power for the light of the laser beam 7 used, so that injuries may arise in the case of contact of these skin deviations with the light of the laser beam 7. The use of the fifth processor 73 and the sixth processor 75 provides an automatic protection against such injuries.

In the embodiment shown in FIG. 4, the fourth processor 59 determines the output signals $u_{M1}$, and $u_{M2}$ in accordance with a predetermined mathematical relation between the output signals $U_{M1}$, $u_{M2}$ and the desired target position 9 of the laser beam 7 as determined by the third processor 57. Said mathematical relation is, for example, a linear function or a function of a higher degree comprising a number of coefficients. As a result of temperature fluctuations or other factors, deviations of the target position 9 resulting from a predetermined value of the output signals $U_{M1}$, $U_{M2}$ may arise. Such deviations can lead to a reduced efficiency of the hair-removing device 1 and to skin irritations or damages. To reduce or avoid such deviations and provide a very accurate positioning of the laser beam 7 on the skin 11 by the mirrors 19, 21, the control unit 17 further comprises a calibration member 81 for calibrating said predetermined mathematical relation on the basis of a measured relation between the output signals $u_{M1}$, $u_{M2}$ and an actual position of the laser beam 7 on the skin 11. Said calibration, for example, constitutes a re-calculation of said coefficients of the predetermined mathematical relation on the basis of the measured relation between the output signals $u_{M1}$, $u_{M2}$ and the actual position of the laser beam 7 on the skin 11, and is carried out by the control unit 17, for example, each time the hair-removing device 1 is started or each time after a predetermined time interval. To carry out said calibration, the mirrors 19, 21 are consecutively positioned in a predetermined number of calibration positions. For this purpose, the fourth processor 59 consecutively supplies a predetermined number of output signals $u_{M1}$, $u_{M2}$ having predetermined values. In each calibration position of the mirrors 19, 21, the actual position of the laser beam 7 on the skin 11 is determined by means of a seventh processor 83 of the control unit 17, which determines said actual position from the image detected by the image sensor 47. For this purpose, as shown in FIG. 4, the seventh processor 83 receives the signal $u_S$ supplied by the image sensor 47, and supplies a signal $u_{AP}$ corresponding to the actual position of the laser beam 7 on the skin 11 to the calibration member 81. After the determination of the actual position of the laser beam 7 in each calibration position of the mirrors 19, 21, the calibration member 81 supplies a signal $u_{CAL}$ corresponding to the re-calculated coefficients of the predetermined mathematical relation to the fourth processor 59. During said calibration process, the fourth processor 59 activates the laser source 3 at a comparatively low energy density via a suitable value of the signal $u_L$. Said energy density is as low as possible, but such that the spot of the laser beam 7 on the skin II is still sufficiently bright to be detected by the image sensor 47. In this manner, skin irritation or damage are prevented during the calibration process, and the energy consumption of the laser source 3 is limited. It is noted, that the invention also comprises embodiments, in which the actual position of the laser beam 7 on the skin 11 is determined in a similar manner from the image detected by the image sensor 47, but in which the laser beam manipulator 5 is corrected in a different manner. The control unit 17 may, for example, alternatively be provided with a feed back control circuit comprising a comparator, which compares the actual position of the laser beam with the desired target position and supplies an error signal, and a PID regulator, which determines the output signals $u_{M1}$ and $u_{M2}$ on the basis of said error signal in such a manner that the measured actual position equals the desired target position. The invention also comprises embodiments, in which the actual position of the laser beam on the skin is not determined by means of the image sensor, but by means of a separate sensor means such as, for example, sensors which directly measure the angular positions of the mirrors 19, 21.

As FIG. 1 shows, the hair-removing device 1 according to the invention further comprises a handle 181 by means of which the user can place the hair-removing device 1 on the skin 11 to be treated and can displace it over the skin 11. As was described above, the portion of the skin 11 present below the opening 33 only is treated. After the treatment of said portion of the skin 11, the user should displace the hair-removing device 1 into a next position on the skin 11.

The hair-removing device 1 may be provided, for example, with an acoustic source which is triggered by the control unit 17 and which produces an acoustic signal the moment the treatment of the portion of the skin 11 present below the opening 33 has been completed. The hair-removing device 1 may alternatively be provided, for example, with electrical drive means controlled by the control unit 17 for the automatic displacement of the hair-removing device 1 over the skin 11 to be treated, instead of with such an acoustic source.

Figure 7:
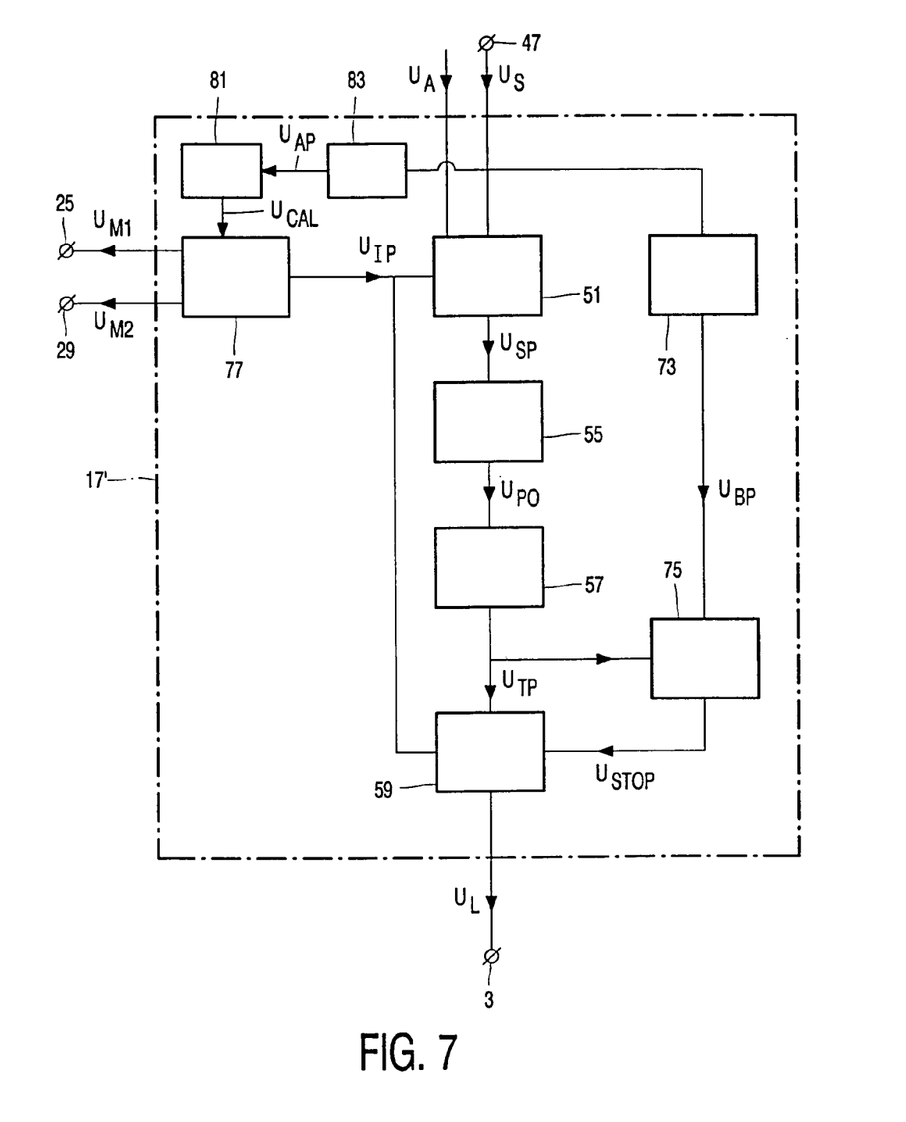

FIG. 7 shows a control unit 17' of a further embodiment of a hair-removing device 1' according to the invention. Apart from the control device 17', the hair-removing device 1' has a composition comparable to that of the hair-removing device 1 according to the invention shown in FIG. 1. Components of the hair-removing device 1' corresponding to components of the hair-removing device 1 described above have been given the same reference numerals in FIG. 7, and the description below will deal exclusively with the differences between the control units 17 and 17' and the resulting differences in operation between the hair-removing devices 1 and 1'.

Figure 8:
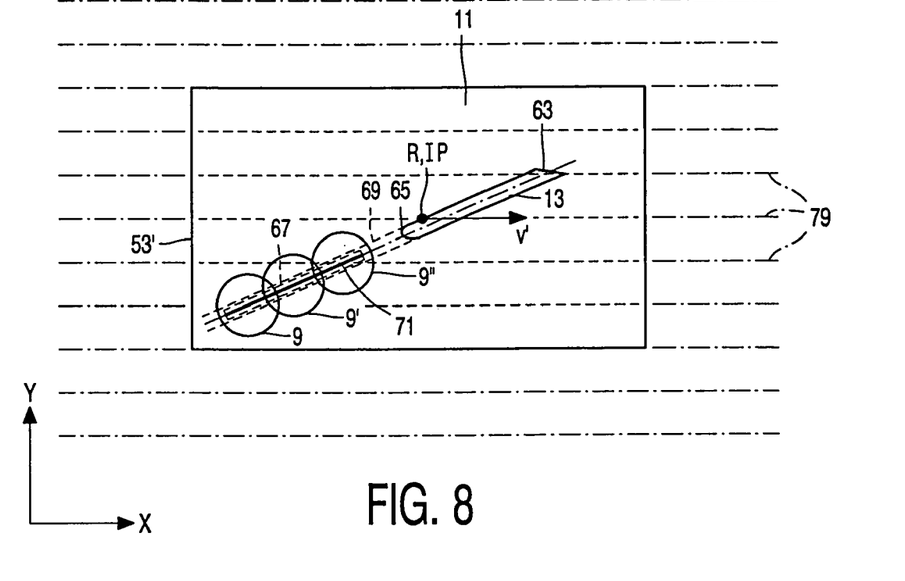

As FIG. 7 shows, the control unit 17' likewise comprises a first processor 51, a second processor 55, a third processor 57, a fourth processor 59, a fifth processor 73, and a sixth processor 75. The control unit 17' comprises furthermore a seventh processor 77 which determines the first output signal $u_{M1}$ and the second output signal $u_{M2}$ by means of which the control unit 17' controls the first tilting mirror 19 and the second tilting mirror 21 of the laser beam manipulator 5, respectively. The control unit 17' likewise comprises a calibration member 81 and an eighth processor 83, which correspond with the calibration member 81 and the seventh processor 83 of the control unit 17 and which cooperate with the image sensor 47 and the seventh processor 77 in a manner similar to the manner in which the calibration member 81 and the seventh processor 83 of the control unit 17 correspond with the image sensor 47 and the fourth processor 59. The seventh processor 77 determines the output signals $u_{M1}$ and $u_{M2}$ such that the tilting mirrors 19 and 21 are adjustable into a sequence of consecutive positions which correspond to a regular sequence of virtual positions of the laser beam 7 on the portion of the skin 11 below the opening 33, in particular with a displacement of the virtual position of the laser beam 7 with a predetermined velocity v' in accordance with a number of lines extending parallel to the X-direction and following one another as seen in the Y-direction. As FIG. 7 shows, the seventh processor 77 here supplies to the first processor 51 an electrical signal $u_{IP}$ which corresponds to the instantaneous virtual position IP of the laser beam 7. The first processor 51 generates from the signals $u_S$ and $u_{IP}$ a partial region 53' of the image 49 which is diagrammatically shown in FIG. 8 and which has dimensions determined by a previously determined average distance between the hairs 13 present on the skin 11 and a previously determined length of the hairs 13. The dimensions of the partial region 53' can be set by the user by means of an adjustment member which is not shown and which supplies to the first processor 51 an electrical signal $u_A$ which corresponds to the dimensions of the partial region 53' as set by the user. The first processor 51 generates the partial region 53' such that a reference position R in the partial region 53' shown in FIG. 8, in particular a central position of the partial region 53', corresponds continually to the instantaneous virtual position IP of the laser beam 7. The partial region 53' thus follows the rectilinear displacement of the instantaneous virtual position IP of the laser beam 7 over the image 49. FIG. 8 also shows a number of lines 79 along which the instantaneous virtual position IP of the laser beam 7 is displaced over the image 49. The first processor 51 supplies to the second processor 55 an electrical signal $u_{SP}$ which corresponds to the partial region 53', and the second processor 55 determines from the signal $u_{SP}$ the position and the orientation in the partial region 53' of the hair 13 present in the partial region 53'. The second processor 55 supplies to the third processor 57 an electrical signal $u_{PO}$ which corresponds to the position and the orientation of the hair 13 in the partial region 53' as determined by the second processor 55, and the third processor 57 determines from the signal $u_{PO}$ the target positions 9, 9', and 9" of the laser beam 7 in the partial region 53'. The third processor 57 supplies to the fourth processor 59 an electrical signal $u_{TP}$ which corresponds to the target positions 9, 9', and 9" of the laser beam 7 as determined by the third processor 57. The fourth processor 59 compares the instantaneous virtual position IP of the laser beam 7 with the target positions 9, 9', and 9" of the laser beam 7 and activates the laser source 3 by means of the output signal $u_L$ during the previously determined pulse duration whenever the instantaneous virtual position IP of the laser beam 7 corresponds to one of the target positions 9, 9', or 9" of the laser beam 7 in the partial region 53'. The fifth processor 73 and the sixth processor 75 in the control unit 17' have functions comparable to those of the fifth processor 73 and the sixth processor 75 in the control unit 17.

An advantage of the hair-removing device 1' with the control unit 17' is that the laser beam manipulator 5 is continually adjusted by the control unit 17' in a regular manner, so that the laser beam manipulator 5 need not have an exceptionally high adjustment accuracy and an exceptionally short adjustment time. The portion of the skin 11 present below the opening 33 is scanned by the laser beam manipulator 5 in a regular manner, and the partial region 53' of the image 49 generated by the control unit 17' follows the virtual position IP of the laser beam 7 on said portion of the skin 11, the target positions 9, 9', and 9" of the laser beam 7 changing continually with respect to the reference point R of the partial region 53'. Good results are obtained in this further embodiment of the hair-removing device 1' when an interspacing is present between the consecutive lines 79 in the image 49 which is equal to or is preferably smaller than the spot diameter of the laser beam 7. However, scanning of all lines 79 present in the image 49 by the laser beam manipulator 5 takes longer than the direct displacement of the laser beam manipulator 5 into the consecutive target positions in the image 49 as in the hair-removing device 1, so that the hair-removing device 1' will have a longer treatment time than the hair-removing device 1 in most cases.

Figure 9:
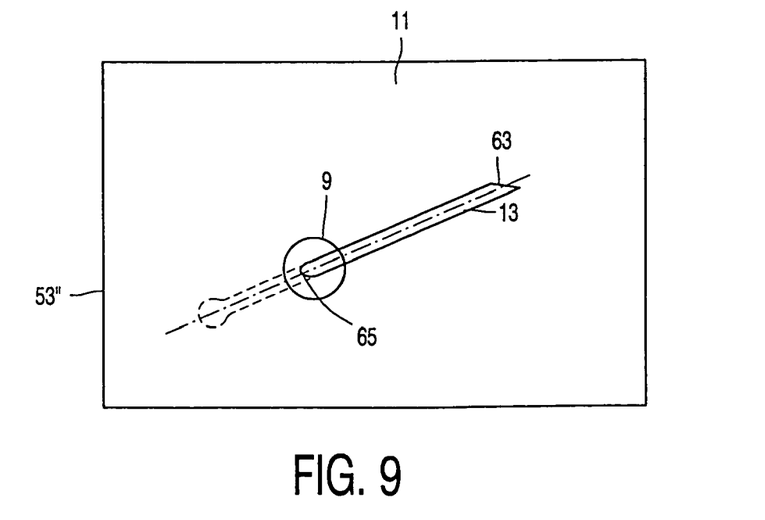

The hair-removing devices 1 and 1' described above are epilation devices by means of which hairs 13 are removed from the skin 11 for a comparatively long period or even permanently. A yet further embodiment of a hair-removing device 1" according to the invention operates as a shaver. The hair-removing device 1" has a construction which is largely identical to the construction of the hair-removing device 1 shown in FIG. 1. The hair-removing device 1" differs from the hair-removing device 1 in that the hair-removing device 1" determines the target position 9 of the laser beam 7 on the skin 11 in a different manner. FIG. 9 diagrammatically shows a partial region 53" of the image 49 of the skin 11 under treatment which is detected by means of the image sensor 47 of the hair-removing device 1". The third processor 57 of the control unit 17 of the hair-removing device 1" determines the target position 9 of the laser beam 7 such that this target position 9 lies on the hair 13 to be removed adjacent the exit position 65 of the hair 13 determined by the second processor 55. The hair 13 is thus burnt through by the laser beam 7 adjacent the exit position 65. The control unit 17 of the hair-removing device 1" can be so programmed that the target position 7 lies flush with or even below the surface of the skin 11, so that a very smooth shaving result is achieved with the hair-removing device 1", which is maintained for a comparatively long period. The hair-removing device 1" may be further provided with an adjustment member by means of which the user can adjust the location of the target position 9 relative to the surface of the skin 11, thus adjusting a desired smoothness. It was found that the burning-through of hairs 13 by means of the laser beam 7 is possible at an energy density of the laser beam 7 which is considerably smaller than the energy density necessary for the epilation of the hairs 13 as described above. The hair-removing device 1" may thus be provided with a comparatively small and inexpensive laser diode with a power of, for example, between 100 mW and 500 mW.

It is noted that the invention also covers a hair-removing device in which the epilation function and the shaving function as described above are combined, in which case the user can select the desired mode of operation, for example by means of an adjustment member. Preferably, the energy density of the laser source is also controllable by means of the control unit of such a hair-removing device, so that the energy density of the laser source can be adapted to the desired mode of operation of the hair-removing device. If the hair-removing device has an epilation function or has been set as an epilation device by the user, the hair-removing device may also be provided, for example, with an automatic shaving function. If the hair-removing device has exclusively an epilation function, in which case exclusively the roots 15 of the hairs 13 are destroyed, the hairs 13 will not disappear from the skin 111 until after some time, so that the desired result is not achieved immediately. If the epilation function of the hair-removing device is automatically combined with a shaving function, it is not only the roots 15 of the hairs 13 which are destroyed, but the hairs 13 are also burnt through adjacent the surface of the skin 11, so that the hairs 13 are immediately removed from the skin 11 and the desired result is achieved instantaneously.

It is further noted that a hair-removing device according to the invention may be provided with a different type of laser beam manipulator instead of the laser beam manipulator 5 having the two tilting mirrors 19 and 21 as described above. Thus, for example, the two tilting mirrors 19 and 21 may be replaced by a single tilting mirror which is tiltable about two mutually perpendicular tilting axes. Instead of a laser beam manipulator with one or more than one tilting mirror, for example, a laser beam manipulator may alternatively be used which is provided with an object holder which is displaceable in two mutually perpendicular directions, in which case the laser source and the image sensor are fastened to said object holder in fixed positions.

It is further noted that the invention also covers embodiments of the hair-removing device in which a type of image sensor is used different from the image sensor 47 with CCD as described above. An example of such an image sensor is a CMOS image sensor. Such a CMOS image sensor may be provided with a RAM memory, so that part of the control unit or even the entire control unit of the hair-removing device can be integrated with the CMOS image sensor. The construction and manufacture of the hair-removing device are considerably simplified in this manner.

In the embodiments of the hair-removing device according to the invention described above, the control unit determines the target position of the laser beam each time in a partial region of the image of the skin detected by means of the image sensor. It is noted that the invention also relates to embodiments in which the control unit determines the target positions of the laser beam once and for all in the entire image of the skin detected by the image sensor. Such embodiments, however, require a control unit with a comparatively great calculation capacity and memory capacity.

It is finally noted that the invention also relates to embodiments of the hair-removing device in which the positions of the hairs on the skin under treatment are not detected by means of reflected light of a separate illumination member, such as the illumination member 35 described above, but in which the positions of the hairs are detected by means of reflected light from the laser beam. The skin to be treated is scanned by means of the laser beam in such embodiments, during which the laser beam has a comparatively low energy density, which energy density of the laser beam is temporarily raised in the target position. The reflected light of the laser beam may be detected in such embodiments, for example, by means of a simple photodetector which detects only the intensity of the reflected light of the laser beam. The expression "image sensor for detecting an image of at least a portion of the skin" in the claims therefore also relates to such a comparatively simple photodetector. Such a method of detection may be used in a comparatively simple manner in the hair-removing device 1' described with reference to FIG. 7, but it may also be used in, for example, a hair-removing device provided with a laser beam manipulator with a displaceable object holder as described above.

The invention claimed is:

1. A hair-removing device comprising a laser source, an adjustable laser beam manipulator for positioning a laser beam supplied by the laser source during operation in a target position on a skin to be treated, and an image sensor for detecting an image of at least a portion of the skin, wherein the laser source is controllable by an electrical control unit; which control unit during operation determines the target position of the laser beam as a function of a position and/or orientation on the skin of a hair to be removed as determined from the image by the control unit, and which control unit activates the laser source the moment the laser beam manipulator is in a position which corresponds to the target position of the laser beam wherein the control unit determines from the position and orientation on the skin of the hair to be removed, as determined from the image, a region on the skin below which a root of the hair will be present with a predetermined degree of probability, the control unit determining at least one target position on the skin in said region.

2. A hair-removing device comprising a laser source, an adjustable laser beam manipulator for positioning a laser beam supplied by the laser source during operation in a target position on a skin to be treated, and an image sensor for detecting an image of at least a portion of the skin, wherein the laser source is controllable by an electrical control unit; which control unit during operation determines the target position of the laser beam as a function of a position and/or orientation on the skin of a hair to be removed as determined from the image by the control unit, and which control unit activates the laser source the moment the laser beam manipulator is in a position which corresponds to the target position of the laser beam wherein the control unit determines an exit position on the hair, where the hair issues from the skin, from the position and orientation on the skin of the hair to be removed as determined from the image, the control unit equalizing the target position of the laser beam with position on the hair adjacent said exit position.

* * * * *